United States Patent

Ferguson

[11] 4,169,950
[45] Oct. 2, 1979

[54] AMINO-HYDROXY-ALKYL SULFONIC ACID ZWITTERIONS

[75] Inventor: Wilfred J. Ferguson, University Heights, Ohio

[73] Assignee: Research Organics, Cleveland, Ohio

[21] Appl. No.: 858,616

[22] Filed: Dec. 8, 1977

[51] Int. Cl.² ............................................. C07D 295/10
[52] U.S. Cl. .................................. 544/158; 544/398; 260/501.12
[58] Field of Search .................................. 544/158, 398

[56] References Cited

U.S. PATENT DOCUMENTS 2,109,401 2/1938 Nicodemus et al. ............... 544/158

OTHER PUBLICATIONS

Good et al., "Biochemistry," vol. 5, No. 2, (1966), pp. 467–477.

Primary Examiner—Alan L. Rotman
Assistant Examiner—R. W. Ramsuer
Attorney, Agent, or Firm—Maky, Renner, Otto & Boisselle

[57] ABSTRACT

Novel amino-hydroxy-alkylene sulfonic acid zwitterions are described which have the general formulas

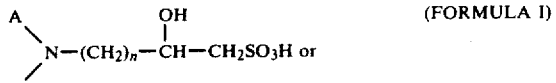

(FORMULA I)

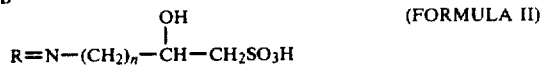

(FORMULA II)

wherein
  A and B are each independently a hydrogen atom, an aliphatic, cycloaliphatic or hydroxyaliphatic group,
  n is one or two, and
  R=N is a cyclic radical comprising one or two ring nitrogen atoms, zero or one ring oxygen atoms and the remainder of the ring being carbon atoms, and water soluble salts of said acids. These organo-sulfonic acid compounds are useful as hydrogen ion buffers in biological research and particularly for tissue culture.

7 Claims, No Drawings

AMINO-HYDROXY-ALKYL SULFONIC ACID ZWITTERIONS

BACKGROUND OF THE INVENTION

This invention relates to new and improved hydrogen ion buffers useful for biological research, and more particularly, to new aminosulfonic acid compounds having superior characteristics as buffers in such applications.

There has been a continuing need for hydrogen ion buffers between pH of six and eight since not many buffers have been known which are completely suitable in this pH range. These types of buffers are used extensively in biological research, and frequently, biologists and chemists have had to select buffers having some undesirable reactivity or toxicity, or buffers of questionable effectiveness because of the shortage of suitable and desirable buffers. For example, phosphate has been used as a buffer even though it has poor buffering capacity above pH 7.5 and tends to precipitate most polyvalent cations in many systems. Another commonly used buffer, tris-(hydroxymethyl)aminomethane (Tris) has poor buffering capacity below pH 7.5. Moreover, it is a primary aliphatic amine of considerable reactivity and, therefore, is often inhibitory. Often the biologist has been forced to ignore the side effects of buffers in view of the unavailability of alternative buffers.

A group of hydrogen ion buffers covering the range pK$_a$ of 6.15-8.35 has been discussed by Professor Norman E. Good in *Biochemistry*, Volume 5, No. 2, pages 467-477, 1966. Some of these may be generally classified as substituted-amino alkylene sulfonic acid zwitterions.

There continues to be a need, however, for additional hydrogen ion buffers, and particularly buffers having increased water solubility and slightly lower pK$_a$ values which may fall within a more favorable physiological pH range. In this application, pK$_a$ is used to represent the pH of the midpoint of the buffering range of the particular composition.

Higher molecular weight organic aminosulfonic acids useful as washing and cleaning agents are described in U.S. Pat. No. 3,196,173. The acids have the general formula R$^1$(R$^2$)NR$^3$SO$_3$X wherein R$^1$ is an aliphatic, cycloaliphatic, or aliphatic-aromatic group containing at least eight carbon atoms, R$^2$ is a hydroxy-substituted aliphatic group, R$^3$ may be ethylene, propylene or 2-hydroxy propylene and X may be hydrogen, alkali metals or a substituted amine.

SUMMARY OF THE INVENTION

New compositions are prepared and described which are useful as hydrogen ion buffers in a desirable pK$_a$ range for biological research. These new compounds are organo-sulfonic acid compounds having the general formulas

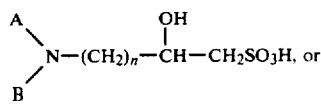 (FORMULA I)

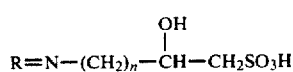 (FORMULA II)

wherein

A and B are each independently a hydrogen atom, an aliphatic, cycloaliphatic or hydroxyaliphatic group, n is one or two, and R=N is a cyclic radical comprising one or two ring nitrogen atoms, zero or one ring oxygen atoms and the remainder of the ring being carbon atoms, and water soluble salts of said acids.

DESCRIPTION OF THE PREFERRED EMBODIMENTS

The organo-sulfonic acid compounds of the invention have the general formulas

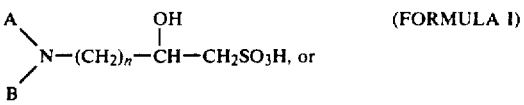 (FORMULA I)

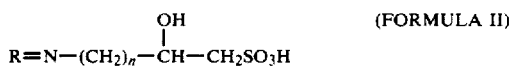 (FORMULA II)

wherein

A and B are each independently a hydrogen atom, an aliphatic, cycloaliphatic, or hydroxyaliphatic group, n is one or two, and R=N is a cyclic radical comprising one or two ring nitrogen atoms, zero or one ring oxygen atoms and the remainder of the ring being carbon atoms, and water soluble salts of said acids.

An important feature of the compounds of the invention is the presence of the hydroxyl group on the carbon atom which is adjacent to the carbon atom being the sulfonic acid group.

Compounds of the type represented by Formulas I and II generally can be prepared by reacting a mixture of a nitrogen-containing compound which may be represented by the formulas

or R=N—H, wherein A, B and R=N are as defined above, with a water-soluble salt of 3-halo-2-hydroxy propyl sulfonate or 4-halo-2-hydroxyl butyl sulfonate in water at reflux temperature. The sodium salts of the respective chlorosulfonates are preferably used in the reaction since these are commercially available or easily prepared. After cooling, one method which has been used to recover the reaction product involves passing the reaction mixture through a hydrogen form of a cation exchange resin such as a sulfonic acid resin (Dowex 50). The product, if cationic in nature, is absorbed on the resin, and all of the by-products and halogen are washed through the column. A solution of ammonium hydroxide is passed through the column to elute the product. The basic solution of the ammonium salt of the buffer is concentrated, adjusted to a pH of about 5 with acid and diluted with alcohol whereupon the product is precipitated.

In Formula I, A and B preferably are hydroxyaliphatic groups containing up to about 4 carbon atoms in the aliphatic group. A and B also may be aliphatic groups containing up to about four carbon atoms such as methyl, ethyl, propyl and butyl, or cycloaliphatic groups, preferably cyclohexyl and substituted cyclohexyl groups.

The cyclic radical R=N of Formula II preferably is a piperazinyl or morpholinyl group. The piperazinyl group may be represented by the general formula

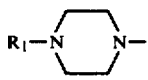

(FORMULA III)

wherein $R_1$ is a hydrogen atom, an alkyl or hydroxyalkyl group containing up to about five carbon atoms, or —$(CH_2)_n$—CH(OH)—$CH_2SO_3H$.

The morpholinyl group in Formula II can have the general formula

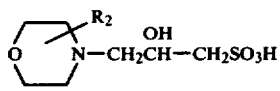

(FORMULA IV)

wherein $R_2$ is a hydrogen atom or an alkyl or a hydroxyalkyl group containing up to about five carbon atoms in the alkyl group.

The following specific examples illustrate the method of preparing some of the compositions of the invention.

EXAMPLE 1

3-[N-(bis-hydroxyethyl)-amino]-2-hydroxypropyl sulfonic acid

A mixture of 210.3 gms. (2 moles) of diethanol amine, 500 cc of water, 196.5 gms (1 mole) of sodium-3-chloro 2-hydroxypropyl sulfonate is charged to a 1-liter, 2-neck flask equipped with a stirrer and a condenser. The mixture is stirred vigorously and heated at the reflux temperature for 3 hours. After cooling to 25° C., the solution is passed through a column of Dowex 50, hydrogen form, cation exchange resin to remove sodium cations and to form the free acid. The eluate from the column is evaporated to a thick oil under vacuum. Upon diluting with alcohol, the product crystallizes from the solution, is filtered and washed with alcohol and dried. About 150 gms of lustrous white plates melting at 189°-190° C. are obtained. Analysis of the product indicated a carbon content of 32.97%, hydrogen content of 7.15% and a nitrogen content of 6.07%. The calculated values are carbon, 34.5%; hydrogen, 7.0%; and nigrogen, 5.8%. The $pK_a$ of the product at 20° C. is 7.6.

EXAMPLE 2

3-[N-(tris-hydroxymethyl) methyl amino]-2-hydroxypropane sulfonic acid

A mixture of 242.28 gms (2 moles) of tris (hydroxymethyl) amino methane, 500 cc. of water and 196.5 gms (1 mole) of sodium 3-chloro-2-hydroxy propyl sulfonate is charged to a 1-liter, 2-neck flask equipped with stirrer and condenser. The mixture is stirred vigorously at reflux for 3 hours. After cooling, the product is recovered in the manner described in Example 1. A yield of 160 gms of the white product melting at 226° C. (with decomposition) is obtained. This product is found to have a carbon content of 32.7%, a hydrogen content of 6.52% and a nitrogen content of 5.39%. The calculated values are 32.4% carbon; 6.6% hydrogen; and 5.4% nitrogen. The $pK_a$ of the product at 20° C. is 7.7.

EXAMPLE 3

N-hydroxyethyl piperazine-N'-2 hydroxypropyl sulfonic acid

A mixture of 260.4 gms (2 moles) of N-beta-hydroxyethyl piperazine, 300 cc. of water and 196.5 gms (1 mole) of sodium-3-chloro-2-hydroxypropyl sulfonate is charged to a 1-liter, 2-neck flask equipped with a stirrer and condenser. The mixture is stirred and refluxed for 2 hours, and after cooling to room temperature, the solution is passed through a Dowex 50, hydrogen form, cation exchange column. The product, being cationic in nature, is absorbed on the resin and all by-products and halogen is washed through the column. A solution of ammonium hydroxide (2 molar) is passed through the column to elute the product. The basic solution of ammonium salt of the buffer is concentrated in oil under vacuum, adjusted to pH 5 with glacial acetic acid and diluted with alcohol whereupon the product precipitates. After filtering, washing with alcohol and drying, a yield of 140 gms of white material melting at 158°-160° C. is obtained. Analysis of the white material indicates a carbon content of 40.27%, a hydrogen content of 7.69% and a nitrogen content of 10.4%. Calculated values are carbon, 40.22%; hydrogen, 7.5%; and nitrogen 10.4%. The product has a $pK_a$ at 20° C. of 7.9.

EXAMPLE 4

Piperazine-N,N'-2-hydroxypropyl sulfonic acid (dihydrate)

A mixture of 86.14 gms (1 mole) of piperazine, 300 cc. of water and 393 gms (2 moles) of sodium-3-chloro-2-hydroxypropane sulfonate is charged to a 1-liter 3-neck flask equipped with stirrer, condenser and additional funnel. The mixture is stirred at the reflux temperature for 30 minutes and a solution of 80 gms (2 moles) of sodium hydroxide in 200 cc. of water is placed in the additional funnel and added slowly to the refluxing reaction. After the addition is completed, the solution is refluxed an additional hour and cooled to room temperature. The solution is slowly acidified to pH 1.5 with concentrated 12 normal hydrochloric acid, and the very insoluble double zwitterion precipitates. The product is filtered, washed with water and dried. A yield of 200 gms of a white crystalline material melting with decomposition at 320° C. is obtained. Analysis of the product indicated a carbon content of 29.74%, a hydrogen content of 6.56% and a nitrogen content of 7.06%. The calculated values are carbon, 30.1%; hydrogen, 6.5%; and nitrogen, 7.06%. The $pK_a$ of the product at 20° C. is 7.85.

EXAMPLE 5

4-[N-(bis-hydroxyethyl)-amino]-2-hydroxybutyl sulfonic acid

This product is prepared in accordance with the procedure of Example 1, except that 210 gms (1 mole) of sodium-4-chloro-2-hydroxybutyl sulfonate is used in lieu of the corresponding hydroxypropyl sulfonate.

EXAMPLE 6

3-(N-morpholino)-2-hydroxypropyl sulfonic acid

A mixture of 174.24 gms (2 moles) of morpholine, 300 cc. of water and 196.5 gms (1 mole) of sodium-3-chloro-2-hydroxypropyl sulfonate is charged to a 1-liter, 2-neck flask equipped with stirrer and condenser. The suspension is stirred vigorously and refluxed for 3 hours. After cooling to about 25° C., the solution is passed through a column of Dowex 50 in order to remove sodium cations and form the free acid. The eluate from the column, containing the product, is evaporated to a thick oil under vacuum. Upon diluting with alcohol, the product, in the form of a zwitterion, crystallizes readily. The product is filtered, washed with alcohol and dried. The yield is 160 gms of a white material melting at 280° C. with decomposition. Analysis of the product indicates a carbon content of 37.38%, a hydrogen content of 6.74%, and a nitrogen content of 6.24%. The calculated values are carbon, 37.3%; hydrogen, 6.7%; and nitrogen, 6.2%. The $pK_a$ of this product at 20° C. is 6.95.

EXAMPLE 7

3-[N-(α,α-dimethyl hydroxyethyl)amino]-2-hydroxypropyl sulfonic acid

This composition is prepared in accordance with the procedure of Example 2, except that 274 gms (2 moles) of 2-amino-2-methyl propanol (AMP) are used in lieu of the tris-(hydroxymethyl) amino methane.

EXAMPLE 8

3-[N-(bis-cyclohexyl)-amino]-2 hydroxypyropyl sulfonic acid

This compositon is prepared in accordance with the procedure of Example 1 except that 362.6 gms. of dicyclohexyl amine are used in lieu of the diethanol amine.

EXAMPLE 9

3-[N-methyl, N-cyclohexyl amino]-2-hydroxypropyl sulfonic acid

This composition is prepared in accordance with the procedure of Example 1 except that 226.4 gms (2 moles) of N-methyl-cyclohexyl amine are used in lieu of the diethanol amine.

The above described amino sulfonic acids particularly are useful as hydrogen ion buffers in biological research. For example, the zwitterionic buffers of the present invention are useful in the Hill reaction and in the phosphorylation-coupled oxidation of succinate by bean hypocotyl mitochondria. The compositions also are useful in increasing the rate of protein synthesis in cell-free bacterial preparations.

The zwitterion compositions of the invention are useful as buffers in tissue culture media and in some media systems some of the amino sulfonic acids of the invention are satisfactory replacements for or better than the established sodium bicarbonate:carbon dioxide buffer system. Some of the compositions of the invention also compare satisfactorily to the effect of 4-(2-hydroxyethyl)-1-piperazine-ethanesulfonic acids (HEPES). A discussion of and Examples of cell and tissue culture media are found in Paul, *Cell and Tissue Culture*, Chapter VI (5th ed. 1975), and these discussions and examples are hereby incorporated by reference.

In order to determine and demonstrate the utility of the compositions of the invention as cell and tissue culture buffers, the effectiveness of two of the compositions (products of Examples 6 and 3) were evaluated and compared to the standard $NaHCO_3:CO_2$ system. The cell lines used in the tests were NIL B, a hamster fibroblast line; SV-NIL, an SV40-virus transformed line derived from NIL B; and BALB/C 3T3, a mouse embryo tissue. The cells were seeded into T-flasks (screw-capped polystyrene flasks) with a 25 cm² area. On the control flask ($CO_2$ atmosphere), the cap was kept loose to allow gas circulation while the caps on the experimental culture flasks were screwed on tightly. The medium used in these tests was Eagle's MEM 4X (see pages 108-112 of Paul, *Cell and Tissue Culture*, 5th Edition, 1975), in an Earle's salt solution (page 95 of same text) modified to contain 2.2 g/l of bicarbonate for the experimental buffers. The control was not so modified. The control flask was incubated at 37° C. in an atmosphere of 5% $CO_2$ in air whereas the other flasks were incubated at 37° C. in an air atmosphere. The medium was changed every other day.

At appointed times, triplicate flasks were harvested using trypsin, and the approximate cell population was determined using a Coulter electronic particle counter. These tests results indicated that for the buffers tested in the selected media, the product of Example 6 was not as good as the $NaHCO_3:CO_2$ system but about as good as HEPES. The product of Example 3 was as good as, if not better than, the control and the known buffer HEPES in effectiveness in promotion of cell growth for the cells tested. The results of the tests comparing the effectiveness of the product of Example 3 with HEPES and the $NaHCO_3:CO_2$ system on the three cell types described above are summarized in the following Tables. The results which are average values indicate no toxicity of the buffers as compared to the carbonate system and the general improvement in cell growth utilizing the product of Example 3 as a buffer.

TABLE I

Effect of Buffers on Growth of 3T3 Cells

| Time/(Hrs.) | Number of Cells per cm² | | |
|---|---|---|---|
| | Control[1] | HEPES[2] | Prod. of Ex 3[3] |
| 0 | 1000 | 1000 | 1000 |
| 12 | 310 | 640 | 520 |
| 24 | 220 | 400 | 280 |
| 36 | 175 | 300 | 310 |
| 48 | 115 | 230 | 330 |
| 60 | 90 | 280 | 360 |
| 72 | 84 | 380 | 450 |
| 84 | 190 | 760 | 805 |
| 88 | — | 1010 | 1015 |

[1]Minimum Cell Population, about 750 at 70 hrs.
[2]Minimum Cell Population: about 220 at 50 hrs.
[2]Minimum Cell Population: about 280 at 22 hrs.

TABLE II

Effect of Buffers on Growth of SV-NIL Cells

| Time/(Hrs.) | Number of Cells per cm² | | |
|---|---|---|---|
| | Control[1] | HEPES[2] | Prod. of Ex 3[3] |
| 0 | 1000 | 1000 | 1000 |
| 12 | 310 | 440 | 470 |
| 24 | 250 | 200 | 220 |
| 36 | 340 | 230 | 290 |
| 48 | 530 | 260 | 440 |
| 60 | 960 | 380 | 680 |
| 72 | 1100 | 580 | 1000 |
| 84 | 1110 | 940 | 1120 |
| 90 | 1110 | 1040 | 1200 |

[1]Minimum Cell Population: about 200 at 16 hrs.
[2]Minimum Cell Population: about 200 at 24 hrs.
[3]Minimum Cell Population: about 200 at 26 hrs.

TABLE III

| | Effect of Buffers on Growth of NIL B Cells | | |
| --- | --- | --- | --- |
| | Number of Cells per cm² | | |
| Time/(Hrs.) | Control | HEPES | Prod. of Ex 3[3] |
| 0 | 1000 | 1000 | 1000 |
| 12 | 370 | 680 | 740 |
| 24 | 370 | 460 | 550 |
| 36 | 640 | 700 | 900 |
| 48 | 1040 | 1010 | 1100 |
| 60 | 2400 | 1160 | 2600 |
| 72 | 4700 | 3000 | 4300 |
| 84 | 7800 | 4800 | 6600 |
| 90–92 | 9800 | 6700 | 9400 |

[1] Minimum Cell Population: about 260 at 16 hrs.
[2] Minimum Cell Population: about 460 at 24 hrs.
[3] Minimum Cell Population: about 550 at 24 hrs.

The embodiment of the invention in which an exclusive property or privilege is claimed is defined as follows:

1. A morpholinyl hydroxyalkalene sulfonic acid having the formula

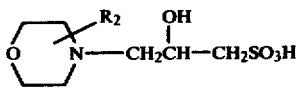

wherein $R_2$ is a hydrogen atom, an alkyl or a hydroxyalkyl group containing up to about 5 carbon atoms in the alkyl group.

2. The acid of claim 1 wherein $R_2$ is a hydrogen atom.

3. An amino sulfonic acid having the general formula

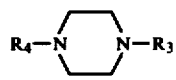

wherein $R_3$ is the group

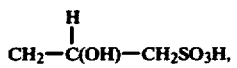

and $R_4$ is the same as $R_3$ or is a hydroxyethyl group.

4. The acid of claim 3 wherein $R_4$ is the same as $R_3$.

5. The acid of claim 3 wherein $R_4$ is a hydroxyethyl group.

6. Amino sulfonic acid compounds having the general formula

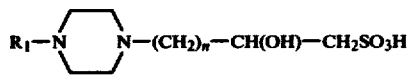

wherein $R_1$ is a hydrogen atom, an alkyl or hydroxyalkyl group containing up to about five carbon atoms, or $-(CH_2)_n-CH(OH)-CH_2SO_3H$, and n is 1 or 2.

7. The compound of claim 6 wherein $R_1$ is a hydroxyalkyl group.

* * * * *